United States Patent [19]
Martin et al.

[11] Patent Number: 6,117,891
[45] Date of Patent: *Sep. 12, 2000

[54] COMPOUNDS AND PHARMACEUTICAL COMPOSITIONS THEREOF FOR ELICITING ANALGESIC EFFECTS

[75] Inventors: Billy R. Martin; Mohamad I. Damaj, both of Richmond, Va.

[73] Assignee: Virginia Commonwealth University, Richmond, Va.

[*] Notice: This patent is subject to a terminal disclaimer.

[21] Appl. No.: 09/257,368

[22] Filed: Feb. 25, 1999

Related U.S. Application Data

[63] Continuation of application No. 08/908,440, Aug. 7, 1997, Pat. No. 5,914,337.

[51] Int. Cl.[7] .................. A61K 31/44; A61K 31/505; A61K 31/435
[52] U.S. Cl. .................. 514/357; 514/256; 514/277
[58] Field of Search .................. 514/357, 256, 514/277

[56] References Cited

U.S. PATENT DOCUMENTS 5,604,231  2/1997  Smith et al. .
5,616,716  4/1997  Dull et al. .

OTHER PUBLICATIONS

P.L. Watson, O. Luanratana, and W. J. Griffin, "The Ethnopharmacology of Pituri", Journal of Ethnopharmacology, 8(1983), pp.303–311.

*Primary Examiner*—William R. A. Jarvis
*Attorney, Agent, or Firm*—Whitham, Curtis & Whitham

[57] ABSTRACT

The present invention relates to treatment of pain with a new class of analgesic compounds. More particularly, the present invention relates to a method for reducing pain of a patient involving administering to a patient an effective amount of an aryl substituted olefinic amine compound. In one aspect, the inventive method of reducing pain in a patient involves use of metanicotine compounds as the analgesic agent.

12 Claims, No Drawings

COMPOUNDS AND PHARMACEUTICAL COMPOSITIONS THEREOF FOR ELICITING ANALGESIC EFFECTS

This application is a continuation of Ser. No. 08/908,440, filed Aug. 7, 1997, now U.S. Pat. No. 5,914,337.

BACKGROUND OF THE INVENTION

The invention is generally related to use of compounds having pharmaceutical properties, and in particular, to compounds useful for eliciting analgesic effects.

Pain has been defined as an unpleasant sensory and emotional experience associated with, or described in terms of, actual or potential tissue damage. See, Stedman's *Concise Medical Dictionary*, p. 545, Prentice Hall, New York, N.Y. (1987). To reduce and/or prevent pain, administration of analgesic compounds to a pain sufferer is desirable to elicit analgesic effects, viz., to produce analgesia and/or reduce response to painful stimuli. Analgesia is a condition in which nociceptive stimuli are perceived but are not interpreted as pain, which usually (but not necessarily always) is accompanied by sedation without loss of consciousness. An analgesic compound is referred to as being an analgetic to the extent it produces analgesia, i.e., altered pain perception. On the other hand, an analgesic is referred to as being an antalgic to the extent it produces a reduced response to painful stimuli. See, Stedman's *Concise Medical Dictionary* (supra), p. 33.

Conventional analgesics have varying degrees of adverse side effects. That is, there is a general unsatisfied need in the prior art of pain relief and reduction for an analgesic agent that is effective while posing less risk of adverse side effects and other pernicious effects to the host. More specifically, it would be highly desirable to provide a pharmaceutical composition incorporating a compound which interacts with nicotinic receptors which has the potential to affect the pain perception and response, but which does not significantly affect those receptors which have the potential to induce side effects (e.g., motor impairment, significant increases in blood pressure or heart rate).

SUMMARY OF THE INVENTION

The present invention relates to treatment of pain with a new class of analgesic compounds. More particularly, the present invention relates to a method for reducing pain of a patient involving administering to the patient an effective amount of an aryl substituted olefinic amine compound.

In one preferred embodiment of the invention, the method of reducing pain in a patient involves use of metanicotine or metanicotine-type compound as the analgesic agent.

The effective amounts of the analgesic compounds necessary to elicit analgesic effects in a host have not been observed to cause adverse side effects or toxicity such as measured by motor impairment. In general, no deleterious effects are caused to the cardiovascular system or skeletal system of the treated patient.

DETAILED DESCRIPTION OF THE PREFERRED EMBODIMENTS OF THE INVENTION

Certain aryl substituted olefinic amine compounds, such as metanicotine, have been demonstrated to be nicotinic receptor agonists possessing high selectively for central nicotinic receptor subtypes relative to peripheral ganglionic and muscular nicotinic receptors. The discovery of the analgesic properties of metanicotine in particular has been confirmed in animal models of pain described hereinafter.

The present invention, in one aspect, relates to use of certain aryl substituted olefinic amine compounds as analgesics having the formula:

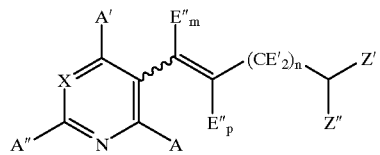

where X is nitrogen, or a carbon bonded to a substituent species characterized as having a sigma m value greater than 0, often greater than 0.1, generally greater than 0.2 and even greater than 0.3; less than 0 and generally less −0.1; or 0; as determined in accordance with Hansch et al., *Chem. Rev.*, Vol. 91, pp. 165–195 (1991); n is an integer of 1 to 7, preferably 2 or 3, and most preferably 2; m and p are integers individually having values of 0 or 1, and preferably are zero; E' represents hydrogen or lower alkyl (e.g., straight or branched alkyl containing one to five carbon atoms, such as methyl, ethyl, or isopropyl) or halo substituted lower alkyl (e.g., straight or branched alkyl containing one to five carbon atoms, such as trifluoro methyl or trichloromethyl); E", if present, represents hydrogen or lower alkyl (e.g., straight or branched alkyl containing one to five carbon atoms, such as methyl, ethyl, or isopropyl) or halo substituted lower alkyl (e.g., straight or branched alkyl containing one to five carbon atoms, such as trifluoro methyl or trichloromethyl); Z' and Z" individually represent hydrogen or lower alkyl (e.g., alkyl containing one to five carbon atoms, such as methyl, ethyl, or isopropyl), and preferably at least one of Z' and Z" is hydrogen; A, A', A" individually represent hydrogen, alkyl (e.g., a lower straight chain or branched alkyl group, including $C_1$–$C_7$, but preferably methyl or ethyl), or a halogen atom (e.g., F, Cl, Br, or I); the wavy line in the structure represents a cis (Z) or trans (E) form of the compound.

X includes N, C—H, C—F, C—Cl, C—Br, C—I, C—NR'R", C—F$_3$, C—OH, C—CN, C—SH, C—SCH$_3$, C—N$_3$, C—SO$_2$CH$_3$, C—OR', C—C(=O)NR'R", C—NR'C(=O)R', C—C(=O)OR', C—OC(=O)R', C—OC(=O)NR'R" and C—NR'C(=O)OR', where R' and R" are individually hydrogen or lower alkyl (e.g., alkyl containing one to five carbon atoms, preferably methyl or ethyl). When X represents a carbon atom bonded to a substituent species, that substituent species often has a sigma value which is between about −0.3 and about 0.75, and frequently between about −0.25 and about 0.6. It is also preferred that A and A' are each hydrogen, while A" is hydrogen, methyl or ethyl, in combination with all E' being hydrogen atoms while m and p are zero (i.e., E" is not present). In another alternate contemplated mode of the invention, Z' can be hydrogen while Z" represents a ring structure, such as cycloalkyl (e.g. cyclopropyl, cyclobutyl, cyclopentyl, cyclohexyl, and so forth), adamantyl, quinolinyl, pyridinyl, pyrinidinyl, phenyl, alkyl or halo substituted phenyl, benzyl, alkyl or halo substituted benzyl; or, alternatively, Z', Z", and the associated nitrogen atom can form a ring structure, such as aziridinyl, pyrollidinyl, piperidinyl, morpholinyl, and so forth.

In a preferred embodiment, the aryl substituted olefinic amine compounds used in this invention are metanicotine and metanicotine-type compounds having the following formula:

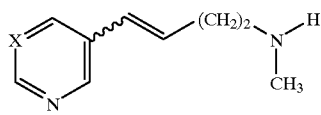

X has the same meaning as defined hereinabove. These metanicotine and metanicotine-type compounds can have the cis (Z) or trans (E) form as indicated by the wavy line in the structure.

Representative compounds useful as the analgesic agent employed in the practice of this invention include, for example, (E)-N-methyl-4-( 3-(pyridin)yl)-3-buten-1-amine (i.e., trans (E)-metanicotine per se, where X is C—H, m and p are zero, n is 2, Z" is methyl, and A, A', A", E' and Z' are hydrogens); (Z)-N-methyl-4-(3-(pyridin)yl)-3-buten-1-amine (i.e., cis(Z)-metanicotine per se); (E) and (Z)-N-methyl-4-(3-(pyridinyl)-2-methyl-3-buten-1-amine; (E)-N-methyl-4-[3-(5-methoxy-pyridin)yl]-3-buten-1-amine; (E)-N-methyl-4-(5-pyrimidinyl)-3-buten-1-amine; (E)-4-[3-(5-methoxypyridin)yl]-3-buten-1-amine; (E)-N-methyl-4-[3-(5-ethoxypyridin)yl]-3-buten-1-amine; (E)-N-methyl-4-[3-(5-amino-pyridin)yl]-3-buten-1-amine; (E)-N-methyl-4-[3-(5-bromo-pyridin)yl]-3-buten-1-amine; (E)-N-methyl-4-[3-(5-hydroxypyridin)yl]-3-buten-1-amine; (E)-N-methyl-4-[3-(5-methoxy-6-methylpyridin)yl]-3-buten-1-amine; (E)-N-methyl-4-[3-(6-methylpyridin)yl]-3-buten-3-amine; (E)and (Z)-N-methyl-5-[3-pyridinyl]-4-penten-1-amine; and (E)-N-(2-propyl)-4-[3-pyridinyl]-3-buten-1-amine, and pharmaceutically acceptable salts of these compounds.

The manner in which the aryl substituted olefinic amine compounds used in the present invention are synthetically produced can vary. Numerous methods and techniques for synthesizing aryl olefinic amine compounds, and particularly, metanicotine and metanicotine-type compounds of the above formulae, that are useful in the practice of this invention are described in detail in U.S. Pat. Nos. 5,604,231 and 5,616,716, which teachings are incorporated herein by reference.

The present invention relates to a method for relieving and preventing pain in a host or patient. In particular, the method comprises administering to a host or patient an amount of a compound selected from the general formulae which are set forth hereinabove that is effective for providing some degree of analgesic effect. These compounds are not normally optically active. However, certain compounds can possess substituent groups of a character so these compounds possess optical activity. Optically active compounds can be employed as racemic mixtures or as enantiomers.

The compounds of the above described formulae can be employed in a free base form or in a salt form (e.g., pharmaceutically acceptable salts, such as chloride, perchlorate, ascorbate, tartrate, fumarate, citrate, maleate, lactate, or aspartate).

The pharmaceutical composition also can include pharmaceutically acceptable additives or adjuncts, such as antoxidants, free radical scavenging agents, buffering agents, steroids, and so forth, to the extent that they do not hinder or interfere with the therapeutic effect desired of the analgesic agent.

The manner in which the compounds can be administered can vary. The compounds can be administered by inhalation (e.g., aerosal form); topically (e.g., lotion form); orally (e.g., in liquid form within a pharmaceutically acceptable aqueous or non-aqueous liquid solvent or carrier); intravenously (e.g., within a dextrose or saline solution); as an infusion or injection (e.g., as a suspension or as an emulsion in a pharmaceutically acceptable liquid or mixture of liquids); transdermally (e.g., using a transdermal patch); or using a suppository or an enema. Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan, and include, for example, injections, tablets, hard gelatin capsules, rectal suspension enemas, and transdermal patches.

The optimum delivery routes for the analgesic compounds described herein in the practice of the inventive method include s.c. injection (i.e., subcutaneous injection); i.t. (intrathecal injection)(e.g., epidural injection in the spinal cord); i.v. injection (i.e., intravenous injection); i.m. injection (i.e., intramuscular injection); and the like, in sterile liquid dosage forms. For non-human recipients, the delivery routes available for the analgesic also further includes i.p. injection (i.e., intraperitoneal injection) and i.c.v. (intracerebroventicular injection). Optimal analgesic effects are observed for the present invention where the analgesic compounds are administered directly into the bloodstream of the host.

The administration of pharmaceutical compositions of the present invention can be intermittent, or at a gradual, or continuous, constant or controlled rate to a warm-blooded animal. In addition, the time of day and the number of times per day that the pharmaceutical formulation is administered can vary. Administration preferably is such that the active ingredients of the pharmaceutical formulation interact with nicotinic receptor sites within the body of the subject that affect the perception of pain and/or the response to painful stimuli. Moreover, the compounds of the present invention, when employed in the effective amounts in accordance with the method of the present invention, are selective to certain relevant nicotinic receptors, but do not cause significant activation of receptors associated with unwanted side effects. Relevant receptor sites can include high affinity sites characteristic of those found in the brain. Specifically, the aryl substituted olefinic amine compounds, such as metanicotine, useful in this invention have been demonstrated to be nicotinic receptor agonists possessing high selectively for central nicotinic receptor subtypes relative to peripheral ganglionic and muscular nicotinic receptors. The receptor binding constants of typical compounds useful in carrying out the present invention generally are greater than 1 nM, often are greater than 200 nM, and frequently are greater than about 500 nM. The receptor binding constants of typical compounds useful in carrying out the present invention generally are less than 10 $\mu$M, often are less than about 7 $\mu$M, and frequently are less than about 2 $\mu$M. Receptor binding constants provide a measure of the ability of the compound to bind to half of the relevant receptor sites of certain cells of patients. See, Cheng, et al., *Biochem. Pharmacol.*, Vol. 22, pp. 3099–3108 (1973).

The dose of the compound is that amount effective to prevent occurrence of the symptoms of pain or to treat some symptoms of pain from which the patient suffers. By "effective amount", "therapeutic amount" or "effective dose" it is meant that amount sufficient to elicit the desired pharmacological or therapeutic effects, thus resulting in effective prevention or treatment of pain. Prevention of pain is manifested by a prolonging or delaying of the onset of pain. Treatment of pain is manifested by a reduction in the symptoms of pain associated with pain or amelioration of the re-occurrence of the symptoms of pain.

The host or patient for the analgesic therapeutic treatment using the analgesic compounds described herein generally are mammalian, such as rodents and humans.

The effective dose can vary, depending upon factors such as the condition of the patient, the severity of the symptoms of pain, and the manner in which the pharmaceutical composition is administered. For human patients, the effective dose of the analgesic compounds of the hereinabove described formulae generally requires administering the compound in an amount of at least about 1, often at least about 10, and frequently at least about 25 mg/24 hr./patient. For human patients, the effective dose of the analgesic compounds requires administering the compound which generally does not exceed about 500, often does not exceed about 400, and frequently does not exceed about 300 mg/hr./patient. In addition, administration of the effective dose is such that the concentration of the analgesic compound within the plasma of the human patient normally does not exceed 500 ng/ml, and frequently does not exceed 100 ng/ml. In rodents, such as mice, the effective dosage of the analgesic compound also can be characterized as ranging from about 1 mg active agent/kg host to about 200 mg active agent/kg host.

In the following examples, objects and advantages of this invention are further illustrated by various embodiments thereof but the details of those examples should not be construed to unduly limit this invention. All parts and percentages therein are by weight unless otherwise indicated.

EXAMPLES

Studies were performed to investigate the analgesic effects of metanicotine compounds. More specifically, the analgesic activity of trans (E) form metanicotine was evaluated in different pain tests in mice. The effects of metanicotine on locomotor activity and body temperature were also evaluated. Nicotine (See, Merck Index, 12th ed. monograph no. 6611) was used as a comparison compound for these investigations.

Experimental Protocol:
1. In Vivo Profile Studies After S.C. Injection

An oxalate salt of trans (E)-metanicotine (i.e., (E)-N-methyl-4-(3-(pyridin)yl)-3-butene-1-amine oxalate) was tested in each of Tail-Flick, Hot-plate and PPQ Tests after s.c. (subcutaneous) injection in male ICR mice. Nicotine was studied as a comparison compound, otherwise using the same experimental protocol. Each of these analgesic effect tests were performed 5 minutes after s.c. injection. The s.c. injections were made into the skin located under the neck area of the test animals.

Detailed descriptions of the protocol of the Tail-Flick, Hot-plate and PPQ analgesic tests, as used in these studies, are set forth below.

Protocols of the Analgesic Effect Tests a. Tail-Flick test:

The apparatus itself contained a light source placed directly above a photocell connected to a timer. The mouse was held under a cloth by the technician conducting the experiment. The tail of the test animal was placed over the photocell and the light was turned on. When the test animal felt the discomfort of the heat from the light, it was freely able to remove its tail from the lamp. The photocell than sensed that the tail had moved and the timer was stopped. The typical nontreatment reaction time for an animal subjected to this test was about 2–4 seconds. This test involved a spinal reflex action similar to the removal of a finger from a hot stove. In treated animals, the latency to remove the tail lengthens in proportion to the analgesic potency of the drug. No animal was allowed to remain under the lamp for greater than 10 seconds to prevent any burns to the tail. No animal was subjected twice to this test.

b. Hot-Plate test

This test was similar to the Tail-flick test; however, the heat source instead was a copper platform heated to either 56° C. or 58° C. A test animal was placed on the platform and the latency to jump or lick a paw was timed in seconds at which time the animals were removed from the platform. Latencies of 2–6 seconds were observed in untreated animals and a cutoff of 30 seconds was used in the 56° C. plate and 20 seconds in the 58° C. plate to avoid any paw damage. This test was not used on any animal incapacitated such that motor function was impaired.

c. P-Phenyl quinone (PPO) test

The mice were injected i.p. with 2 mg/kg PPQ prepared in 4% ethanol. At 10 and 15 minutes later, the mice were observed for a characteristic stretching movement induced by PPQ. Following drug treatment, the number of stretches or the number of animals stretching was reduced in the cases where the drug is an analgesic agent. The reduction in the number of test animals that stretched or the total number of stretches is proportional to the analgesic potency of the drug administered.

Also, in the in vivo profile studies using s.c. injection, the effect of the test compounds on locomotor activity and body temperature were determined in the following manner.

Rectal temperature of the test animals was determined by a thermistor probe (inserted 24 mm) and a digital thermometer (manufactured by Yellow Springs Instrument Co., Yellow Springs, Ohio). Readings were taken immediately before and 30 minutes after the s.c. injection of metanicotine or nicotine. For measuring effect on locomotor activity, the mice were placed into individual Omnitech photocell activity cages (28×16.5 cm), 5 minutes after s.c. administration of a 0.9% saline solution containing the metanicotine or nicotine. Locomotor activity was determined as a total activity count in which each and every interruption of the photocell beams (two banks of eight cells each) caused by movement of the mouse was recorded for a time span of 10 minutes.

The results of the tests are summarized in Table 1 below.

2. Analgesic Effect after Central Administration

In these additional studies, an oxalate salt of trans (E)-metanicotine (i.e., (E)-N-methyl-4-(3-(pyridin)yl)-3-butene-1-amine oxalate) was tested using the Tail-Flick Test after intrathecal (i.t.), and i.c.v. injections in male ICR mice. Nicotine was again studied as a comparison compound, otherwise using the same experimental protocol. The Tail-Flick test was performed 5 minutes after injection.

The protocol of the Tail-Flick test was the same as that described above. The details of the i.c.v. and i.t. methods of injection used in these additional tests are described below.

a. Intracerebroventricularly (i.c.v. injection):

The mice were anesthetized with ether in an inhalation chamber enclosed in a fume hood certified by Environmental Health and Safety as to the ability to clear the small amount of ether fumes which might escape from the chamber. The mice are allowed to completely lose consciousness at which time a transverse incision of 5 mm in length is made in the scalp, followed by injection of the drug through the skull into the lateral ventricle. The procedure was done free-hand in less than 15 seconds and required no restraint of the test animal.

b. Intrathecal (i.t.) injection

Intrathecal injections were performed free-hand into the spinal cord located between the L5 and L6 lumbar space in unanaesthetized male mice. The injection was performed using a 30-gauge needle attached to a glass microsyringe. The injection volume in all cases was 5 μL. The accurate placement of the needle was evidenced by a quick "flick" of the mouse's tail.

The results of these additional tests are summarized in Table 2. It is noted that the s.c. injection results for the Tail-Flick test as obtained in the above-described in vivo profile tests are reproduced in Table 2 for comparison.

TABLE 1

|  | Tail-Flick ED50 (mg/kg) | Hot-plate ED50 (mg/kg) | PPQ test ED50 (mg/kg) | Body temp. ED50 | Locomotor Activity. |
|---|---|---|---|---|---|
| Nicotine | 1.5 | 0.73 | 0.20 | 1.2 | 0.60 |
| Metanicotine | 7.2 | 30% @ 48 | 1.6 | 85 | 2% @ 42 |

*Results are expressed as ED50 values in mg/kg.

TABLE 2

|  | S.C. ED50 (μg/mouse) | I.C.V. ED50 (μg/mouse) | I.T. ED50 (μg/mouse) |
|---|---|---|---|
| Nicotine | 1.5 | 13.5 | 12 |
| Metanicotine | 7.2 | 9.2 | 3.7 |

As seen in the data summarized in Table 1, metanicotine elicited a dose-dependent antinociception in the Tail-Flick and the PPQ tests with $ED_{50}$ values of 7.2 and 1.6 mg/kg, respectively, after s.c. injection. Furthermore, metanicotine's effect in the Tail-Flick test were blocked by mecamylamine and dihydro-β-erythroidine, two nicotinic antagonists. However, naloxone (an opioid antagonist) and atropine (muscarinic antagonist), failed to block metanicotine's effects. As also seen in Table 1, metanicotine elicited a partial antinociceptive effect in the Hot-Plate test after s.c administration. This result indicates an involvement in supra-spinal mechanisms in metanicotine's analgesic effect.

No significant effect (2% decrease at the dose of 42 mg/kg) on locomotor activity occurred after s.c. injection of metanicotine, even at doses 10 to 15-times higher than the $ED_{50}$ determined in the analgesic effect tests (i.e., the Tail-Flick, Hot-Plate, PPQ tests). As seen in Table 1, metanicotine elicited a decrease in body temperatures at very high doses (10 to 15-times higher than the $ED_{50}$ for analgesia. However, this hypothermia was not blocked by mecamylamine, suggesting the involvement of non-nicotinic mechanisms.

As seen in Table 2, in the central administration (viz., the i.c.v. and i.t.) tests performed on the other group of mice, metanicotine injected intrathecally (i.t.) and intracerebroventricularly (i.c.v.) induced a dose-dependent antinociceptive effect in the Tail-Flick test. Contrary to what was found after s.c. injection, metanicotine was more potent than nicotine after i.t. and i.c.v. administration.

Contrary to nicotine, a good separation between the analgesic action (potentially therapeutical effect) and side effects (hypothermia and decrease in locomotor activity) exists for metanicotine. These data suggest that activation of neuronal nicotinic receptors elicits an analgesic effect by metanicotine compounds and that metanicotine compounds represent selective nicotinic agonists that can be exploited as analgesics in the treatment of pain.

While the invention has been described in terms of its preferred embodiments, those skilled in the art will recognize that the invention can be practiced with modification within the spirit and scope of the appended claims.

We claim:

1. A method of eliciting an analgesic effect in a host animal in need thereof, comprising the step of:

administering to said host animal an effective dose of a compound, or a pharmaceutically acceptable salt thereof, having the formula:

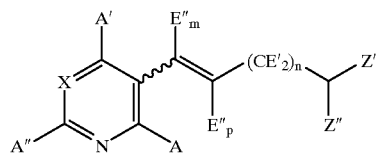

where X is nitrogen, or a carbon bonded to a substituent species characterized as having a sigma m value between about −0.3 and about 0.75; n is an integer value of 1 to 7; m and p are integers individually having values of 0 or 1; E' and E" individually represent hydrogen or a substituted or an unsubstituted alkyl group containing one to five carbon atoms; Z' and Z" individually represent hydrogen or an alkyl group containing one to five carbon atoms; A, A', A" individually represent a hydrogen, an alkyl group, or a halogen atom; and the wavy line in said formula represents a cis (Z) or trans (E) form of said compound.

2. The method of claim 1 wherein said host is a mammal.

3. The method of claim 1 wherein said host is human and said effective dose of said compound ranges from about 1 mg/24 hr./patient to about 500 mg/24 hr./patient.

4. A method of eliciting an analgesic effect in a host animal in need thereof comprising the step of:.

administering to said host animal an effective dose of a compound or a pharmaceutically acceptable salt thereof having the formula;

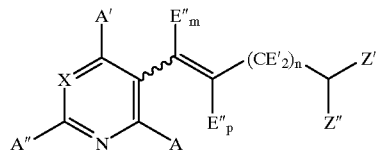

where X is nitrogen, or a carbon bonded to a substituent species characterized as having a sigma m value between about −0.3 and about 0.75; n is an integer value of 1 to 7; m and p are integers individually having values of 0 or 1; E' and E" individually represent hydrogen or a substituted or an unsubstituted alkyl group containing one to five carbon atoms; Z' and Z" individually represent hydrogen or an alkyl group containing one to five carbons; A, A', and A" individually represent a hydrogen, an alkyl group, or a halogen atom; and the wavy line in said formula represents a cis (Z) or trans (E) form of said compound, wherein said step of administration is performed by injection.

5. The method of claim 1 wherein X is selected from the group consisting of N, C—H, C—F, C—Cl, C—Br, C—I, C—NR'R", C—F₃, C—OH, C—CN, C—SH, C—SCH₃, C—N₃, C—SO₂CH₃, C—OR', C—C(═O)NR'R", C—NR'C(═O)R', C—C(═O)OR', C—OC(═O)R', C—OC(═O)NR'R" and C—NR'C(═O)OR' where R' and R" are individually hydrogen or alkyl containing one to five carbon atoms.

6. The method of claim 1 further comprising dispersing or dissolving said compound in a pharmaceutically acceptable carrier prior to the step of administering to said host animal said effective dose of said compound.

7. A method of eliciting an analgesic effect in a host animal in need thereof, comprising the step of:

administering to said host animal an effective dose of a compound, or a pharmaceutically acceptable salt thereof, having the formula:

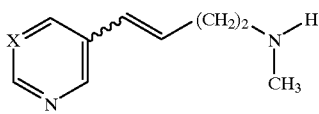

where X is nitrogen, or a carbon bonded to a substituent species characterized as having a sigma m value between about −0.3 and about 0.75; n is 2 or 3, and the wavy line in said formula represents a cis (Z) or trans (E) form of said compound.

8. The method of claim 7 wherein said compound is selected from the group consisting of (E)-N-methyl-4-(3-(pyridin)yl)-3-buten-1-amine), (Z)-N-methyl-4-(3-(pyridin)yl)-3-buten-1-amine), and combinations thereof.

9. The method of claim 7 wherein said host is a mammal.

10. The method of claim 7 wherein said host is human and said effective dose of said compound ranges from about 1 mg/24 hr./patient to about 500 mg/24 hr./patient.

11. A method of eliciting an analgesic effect in a host animal in need thereof, comprising the step of:
  administering to said host animal an effective dose of a compound, or a pharmaceutically acceptable salt thereof, having the formula:

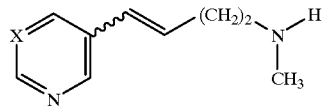

where X is nitrogen, or a carbon bonded to a substituent species characterized as having a sigma m value between about −0.3 and about 0.75; n is 2 or 3, and the wave line in said formula represents a cis (Z) or trans (E) form of said compound, wherein said step of administration is performed by a injection.

12. The method of claim 7 wherein X is selected from the group consisting of N, C—H, C—F, C—Cl, C—Br, C—I, C—NR'R", C—F$_3$, C—OH, C—CN, C—SH, C—SCH$_3$, C—N$_3$, C—SO$_2$CH$_3$, C—OR', C—C(=O)NR'R", C—NR'C(=O)R', C—C(=O)OR', C—OC(=O)R', C—OC(=O)NR'R" and C—NR'C(=O)OR', where R' and R" are individually hydrogen or alkyl containing one to five carbon atoms.

* * * * *